United States Patent [19]

Song

[11] Patent Number: 5,523,505
[45] Date of Patent: Jun. 4, 1996

[54] ZEOLITE-CATALYZED ISOMERIZATION OF SYM-OCTAHYDROPHENANTHRENE TO SYM-OCTAHYDROANTHRACENE

[75] Inventor: Chunshan Song, State College, Pa.

[73] Assignee: The Penn State Research Foundation, University Park, Pa.

[21] Appl. No.: 290,648

[22] Filed: Aug. 15, 1994

[51] Int. Cl.$^6$ .................................... C07C 5/22
[52] U.S. Cl. .................................... 585/481
[58] Field of Search .................................... 585/481

[56] References Cited

U.S. PATENT DOCUMENTS

| | | | |
|---|---|---|---|
| 3,624,173 | 11/1971 | Kirsch et al. | 585/467 |
| 3,715,406 | 2/1973 | Bushick | 585/480 |
| 3,884,986 | 5/1975 | Bushick et al. | 585/481 |
| 4,367,360 | 1/1983 | Gormley | 585/477 |
| 4,376,223 | 3/1983 | Gormley | 585/360 |
| 4,376,224 | 3/1983 | Gormley | 585/360 |
| 4,384,152 | 5/1983 | Handrick et al. | 585/320 |
| 4,384,156 | 5/1983 | Gormley | 585/477 |
| 4,385,194 | 5/1983 | Gormley | 585/477 |

OTHER PUBLICATIONS

Song, et al., Fuel Processing Technology, 34: 157–196 (1993) no month available.

*Primary Examiner*—Sharon Gibson
*Assistant Examiner*—E. D. Irzinski
*Attorney, Agent, or Firm*—Thomas J. Monahan

[57] ABSTRACT

An environmentally benign catalytic process for the production of sym-octahydroanthracene (sym-OHA) from sym-octahydrophenanthrene (sym-OHP) by ring-shift isomerization. Proton-form moralenite or partially dealuminated proton-form mordenite are effective catalysts for the selective formation of sym-OHA from sym-OHP. Y-zeolite and metal-ion exchanged Y-zeolites display lower selectivity towards Sym-OHA. The use of certain solvents can further improve the performance of the Y-zeolites and mordenites, particularly the selectivity of Y-zeolite catalysts. The sym-OHA is an useful product and can be converted by existing methods to various anthracene derivatives which are industrial chemicals in demand.

3 Claims, No Drawings

ZEOLITE-CATALYZED ISOMERIZATION OF SYM-OCTAHYDROPHENANTHRENE TO SYM-OCTAHYDROANTHRACENE

BACKGROUND OF THE INVENTION

The present invention relates to a novel method for the conversion of sym-octahydrophenanthrene (sym-OHP) to sym-octahydroanthracene (sym-OHA) by a zeolite-catalyzed isomerization process.

Anthracene can be produced from sym-OHA. Anthracene and its derivatives such as anthraquinone have large volume uses in the dye industry as an important intermediate, in the chemical industry for making hydrogen peroxide, and in the pulp industry as a pulping agent. Low concentrations of anthracene can be found in coal tar.

Since phenanthrene may be viewed as an isomer of anthracene with respect to the ring-structure, much attention has been given to the conversion of phenanthrene to anthracene. Phenanthrene and its derivatives such as sym-OHP occur in high concentrations in coal-derived liquids, and can be obtained in relatively high yields from coal pyrolysis tars and carbonization tars. The isomerization of sym-OHP to sym-OHA is the key step in the conversion of phenanthrene to anthracene. A more detailed description of the applications of sym-OHA and anthracene are described in a recent publication in C. Song and H. H. Schobert, Fuel Processing Technology, 1993, vol. 34, No. 2, pp. 157–196.

Several U.S. patents have been granted to inventions on the isomerization of sym-OHP to sym-OHA using metal halides such as $AlCl_3$ or $AlBr_3$ (U.S. Pat. No. 4,367,360; 4,376,223; 4,376,224; 4,384,152; 4,384,156; 4,385,194). U.S. Pat. No. 4,376,223 to W. T. Gormley deals with the $AlCl_3$-catalyzed isomerization in the presence of an aryl phenone such as benzophenone, which serves as a promoter. Similarly, several other patents disclosed the same type of $AlCl_3$ catalyzed or $AlBr_3$-catalyzed process but in the presence of an acyl peroxide such as benzoyl peroxide (U.S. Pat. No. 4,376,224 to W. T. Gormley), or in the presence of an aroyl halide such as benzoyl chloride or isophthaloyl chloride (U.S. Pat. No. 4,384,156 to W. T. Gormley), or in the presence of an aralkyl halide such as benzyl chloride (U.S. Pat. No. 4,385,194 to W. T. Gormley). U.S. Pat. No. 4,384,152 to K. Handrick et al. deals with the conversion of phenanthrene to anthracene in three steps: hydrogenation of phenanthrene to produce sym-OHP, isomerization of sym-OHP to sym-OHA using $AlCl_3$ as catalyst, followed by dehydrogenation of sym-OHA to produce anthracene. Among the three steps, the isomerization of sym-OHP into sym-OHA is the most important step. In this invention, $AlCl_3$-catalyzed isomerization of sym-OHP to sym-OHA was carried out in the presence of methylene chloride solvent at a temperature from –30° C. to +5° C. U.S. Pat. No. 4,367,360 to W. T. Gormley deals with the isolation and recovery of $AlCl_3$ catalyst (after the isomerization reaction of sym-OHP into sym-OHA) by using a liquid hydrocarbon solvent such as aliphatic solvent. Because of the highly hygroscopic, water-soluble, and environmentally harmful nature of $AlCl_3$ and $AlBr_3$, it is tedious to separate these metal halide catalysts from the products and to recover the catalysts.

The design of environmentally benign processes has become a significant focus of concern as the chemical industry seeks to alleviate the environmental impact of manufacturing processes. The present invention uses zeolites as catalysts for the isomerization of sym-OHP into sym-OHA. The process is more economical and environmentally benign, whereas metal halides such as $AlCl_3$ or $AlBr_3$ that are used in the previous inventions are environmentally harmful, corrosive, hard to handle and hard to recover. The advantages of the zeolite catalysts that can replace aluminum chloride ($AlCl_3$) are numerous. The zeolites (aluminosilicate) catalysts can catalyze the reaction in place of toxic and corrosive compounds such as $AlCl_3$ and $AlBr_3$ and can be used in a much lower amount, e.g., less than 30 percent of the usual amount of $AlCl_3$. Zeolites can be easily filtered off after the reaction and can be reused because they are not soluble in water or organic solvents. They are not chemical irritants and do not contaminate the products which makes them easy to handle and use.

SUMMARY OF THE INVENTION

A catalyzed ring-shift isomerization process that is environmentally benign for the conversion of sym-octahydrophenanthrene to sym-octahydroanthracene. This process uses a zeolite catalyst at a temperature range of 150° C. to 350° C. which causes the ring-shift isomerization of sym-octahydrophenanthrene to sym-ocmhydroanthracene. The preferable zeolite catalysts are partially dealuminated proton-form mordenites or metal ion-exchanged proton-form Y-zeolites.

DETAILED DESCRIPTION OF THE INVENTION

This invention discloses a process of the zeolite-catalyzed transformation of 1,2,3,4,5,6,7,8-octahydrophenanthrene (sym-OHP) to 1,2,3,4,5,6,7,8-octahydroanthracene (sym-OHA), which is to be defined as ring-shift isomerization. The sym-OHP isomer or the isomer in a mixture can be isomerized into sym-OHA by contacting it with an acidic zeolite catalyst at a temperature in the range of 150° C. to 350° C., preferably within the range of 200° C. to 250° C. Preferred conditions are such that the sym-OHP isomer feed or feed mixture containing sym-OHP is in a liquid phase and is diluted by a hydrocarbon solvent such as mesitylene (1,3,5-trimethylbenzene) or decalin (decahydronaphthalene). Such an isomerization process can be used to produce sym-OHA directly from sym-OHP. Alternatively, such a process can be used to produce sym-OHA from a mixture of products from hydrogenation of phenanthrene, which is the key step in convening phenanthrene derivatives into anthracene derivatives.

Acidic zeolites with relatively large pores such as mordenites (pore dimension: 6.5×7.0 Å) and Y-zeolites (with pore diameters larger than 7 Å) can be used as catalysts for the isomerization of sym-OHP to sym-OHA. The preferable zeolite catalysts are partially dealuminated proton-form mordenites or metal ion-exchanged proton-form Y-zeolites.

Commercial grades of ammonium Y-zeolites, such as those sold by Aldrich Chemical Corporation, Milwaukee, Wis., can be used for preparing metal ion-exchanged Y-zeolites. The metal-ion exchanged Y-zeolites were prepared by mixing an ammonium ion-exchanged Y-zeolite, $NH_4$-Y (SK-Y, $SiO_2/Al_2O_3$ mol ratio: 4.6) and aqueous solutions of $Ni(NO_3)_2 \cdot 6 H_2O$, $Fe(NO_3)_3 \cdot 9H_2O$, and $La(NO_3)_3 \cdot 6H_2O$ respectively. Metal salt solutions were prepared by using commercially available metal salts and deionized water, where the concentration of the metal salt was kept at 0.25 mole per liter. The mixtures were agitated at 85° C. for 2 hours and then filtered. The ion-exchanged zeolites were washed with deionized water, dried at 120° C. for 2 hours and then thermally treated in air at 500° C. for 4 hours. Table 1 shows the properties of the Y-zeolite catalysts (HY, NiHY, FeHY, LaHY) with SiO$_2$/Al$_2$O$_3$ molar ratios ranging from 4.7 to 69.5. The acidity of zeolites was determined as total acidic sites per gram by using temperature-programmed desorption of ammonia. The exceptionally high SiO$_2$/Al$_2$O$_3$ molar ratio (69.5) of FeHy is due to dealumination in the catalyst preparation process.

TABLE 1

Properties of the Y-Zeolite Catalysts

| Catalyst | Precursor ID | Precursor type | Metal Oxide wt % | Final thermal in air | SiO$_2$ to Al$_2$O$_3$ mol ratio | Surface m$^2$/g | Acidity mmol/g |
|---|---|---|---|---|---|---|---|
| HY | SK-Y | NH$_4$-Y | * | 500° C.-4 h | 4.8 | 646 | 0.89 |
| NiHY | SK-Y | NH$_4$-Y | 3.6 wt % NiO | 500° C.-4 h | 4.7 | 665 | 1.07 |
| FeHY | SK-Y | NH$_4$-Y | 4.4 wt % Fe$_2$O$_3$ | 500° C.-4 h | 69.5 | 342 | 0.27 |
| LaHY | SK-Y | NH$_4$-Y | 8.4 wt % La$_2$O$_3$ | 500° C.-4 h | 4.6 | 662 | 0.84 |

*Not Applicable

Poton-form mordenites can be prepared from the thermal treatment of ammonium ion-exchanged Y-zeolites that are commercially available. Partially dealuminated mordenites are also available from several commercial manufacturers such as PQ Corporation, Valley Forge, Pa. and Union Carbide Co., Danbury, Conn. The proton-form mordenites (HM) were prepared by thermal treatment of ammonium ion-exchanged mordenites (NH$_4$-M) in air at 515° C. for 4 hours. Table 2 shows the properties of the mordenite catalysts with SIO$_2$/Al$_2$O$_3$ molar ratios ranging from 17 to 35. The surface area was measured using the nitrogen adsorption method. The SiO$_2$/Al$_2$O$_3$ ratio data was obtained by elemental analysis.

TABLE 2

Properties of the Mordenite Catalysts

| Catalyst | Precursor ID | Precursor type | Final thermal in air | SiO$_2$ to Al$_2$O$_3$ mol ratio | Surface m$^2$/g |
|---|---|---|---|---|---|
| HML8 | LZM8 | NH$_4$-M | 515° C.-4 h | 17 | 480 |
| HM20A | CBV20A | NH$_4$-M | 515° C.-4 h | 20 | 600 |
| HM30A | CBV30A | NH$_4$-M | 515° C.-4 h | 35 | 600 |

Commercially available grades of sym-octahydrophenanthrene, such as sold by TCI America, Portland, Oreg., can be used as a starting material for the conversion to sym-octahydroanthracene. Useful sym-OHP isomer feed or the feed mixture containing sym-OHP can be prepared by hydrogenation of phenanthrene. The solvents that can be used in the isomerization are commercially available organic solvents, such as those from Aldrich Chemical Co., Milwaukee, Wis., or from Fisher Scientific Co., Pittsburgh, Pa.

The isomerization of sym-OHP to sym-OHA occurs by the shift of the ring position on the surface of acidic zeolites, as shown by the formula:

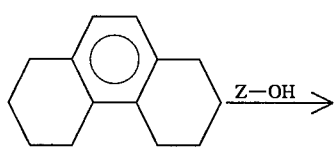

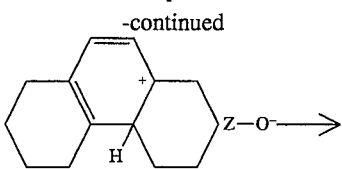

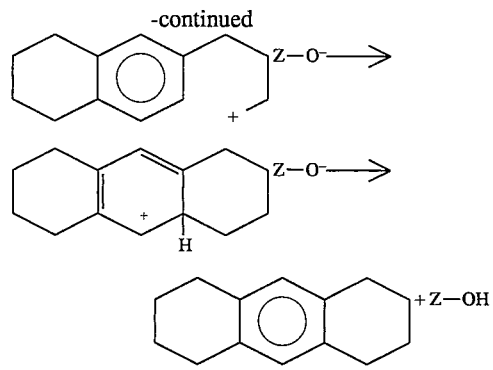

For the conversion of sym-OHP to sym-OHA, it is believed that the first step is an adsorption of sym-OHP on the catalyst surface. After the adsorption, the reaction is initiated by the protonation of the central aromatic ring in sym-OHP. However, the protonated intermediate could lead to several different products due to ring-opening cracking, alkyl chain isomerization, and subsequent cracking. Therefore, the second step is dependent upon whether or not the positive charge is stabilized. For the ring-shift isomerization to occur, the cationic intermediate should be stabilized by nearby alumnina sites. Since zeolite acidity is associated with the aluminum ions, there is a certain level of density of acid sites that is required for effective ring-shift isomerization. In other words, highly aluminum deficient zeolite may not be suitable for this reaction. Therefore, good zeolite catalysts should possess appropriate pore structure and the desired density and strength of the acidic sites for the ring-shift isomerization of sym-OHP. Temperature control is also important. Too low a reaction temperature leads to a slow rate, whereas very high temperature will result in excessive side reactions such as undesirable cracking reactions and undesirable ring-contraction isomerization to form indane-type products. The type of solvent is also influential. The ting-shift isomerization is mechanistically different from the well-known ring-contraction isomerization of hydroaromatic compounds, e.g., conversion of tetralin to 1-methylindane mid sym-OHP to methylindane-type compounds.

The isomerization can be carried out in stainless-steel batch autoclave containing an acidic zeolite catalyst and sym-OHP isomer or its solution in an organic solvent at a temperature in the range of 150° C. to 350° C., under the pressure of $N_2$ gas in the range of atmospheric pressure to 500 psig, for a time period ranging from 10 minutes to 4 hours. The reactors are quenched to room temperature. The products and the catalyst can be separated by simple filtration after the reaction. The catalyst can be recovered easily by washing with acetone solvent, followed by drying in an oven at 110° C. for 2 hours.

All the Y-zeolites shown in Table 1 and mordenite catalysts given in Table 2 displayed certain degree of catalytic activity for sym-OHP conversion at 250° C. The proton-form Y zeolites and metal-ion exchanged Y zeolites, except for FeHY, showed high activity for sym-OHP conversion but low selectivity towards sym-OHA. However, the proton-form mordenites (HML8 and HM30A) afforded a higher yield, and exhibited better selectivity to sym-OHA as compared to the four Y zeolites and another mordenite HM20A. The selectivity with HML8 catalyst at 250° C. is as high as 90 percent at 59 percent conversion. HML8 selectively promotes the ring-shift isomerization of sym-OHP to sym-OHA without enhancing the side reactions at 200°–250° C. HM30A is relatively selective for sym-OHP conversion, but is not as good as HML8. At 300° C., HY and LaHY promoted the conversion to about 90 percent, but the main reactions were cracking reactions and the selectivity to anthracene derivatives was close to zero. HML8, HM20A, and HM30A also gave a higher conversion at higher temperature such as 300° C., but the selectivity to sym-OHA is lower compared to the reaction at 250° C. for 2 hours.

Among the Y-zeolites and mordenites tested, a proton-form mordenite with a relatively lower $SiO_2/Al_2O_3$ molar ratio (about 17) and a nickel ion-exchanged Y-zeolite (with NiO content of 3.6 percent, and a $SiO_2/Al_2O_3$ molar ratio of 4.7) afforded higher a yield of sym-OHA with higher ratio of sym-OHA produce from sym-OHP. The best selectivities towards sym-OHA were obtained with the mordenite catalyst (HML8) at 250° C., which were around 89–91 percent at 58–59 percent conversion of sym-OHP, both in mesitylene and in decalin solvents. In the presence of mesitylene solvent, NiHY also displayed fairly high selectivity to sym-OHA of about 85 percent. In this case, the catalytic activity of NiHY is similar to that of HML8.

The following illustrative examples set forth specific embodiments of the invention. However, the invention is not to be construed as being limited to these embodiments, for there are, of course, numerous possible variations and modifications. Examples 1–4 illustrate the effects of four different Y-zeolite catalysts in the presence of a aliphatic (decalin) solvent. Examples 5–7 show the catalytic effects of three different mordenites with different $SiO_2/_2O_3$ molar ratios in the presence of the decalin solvent. Examples 8–10 illustrate the effects of an aromatic solvent on the performance of three different Y-zeolite catalysts that showed relatively high activity in the presence of the decalin solvent. Examples 11–13 show the catalytic effects of three different mordenites with different $SiO_2/Al_2O_3$ molar ratios in the presence of an aromatic solvent. The results of the examples are listed in Tables 3 and 4. All parts and percentages of the examples as well as throughout the specification are by weight unless otherwise indicated.

TABLE 3

Isomerization of sym-OHP to sym-OHA using zeolites at 250° C. for 2 hours with Decalin Solvent

| Run | Catalyst type | Conv. % | Products (wt % of OHP) | | | | | Select.[a] % |
|---|---|---|---|---|---|---|---|---|
| | | | sym-OHA | THA | THP | DHP | Others[b] | |
| 1 | HY | 78.2 | 26.9 | 3.3 | 5.5 | 0.4 | 4.3 | 38.7 |
| 2 | FeHY | 16.1 | 6.7 | | | 2.1 | 0.7 | 42.0 |
| 3 | NiHY | 83.2 | 21.1 | 4.4 | 6.7 | 0.6 | 50.2 | 30.8 |
| 4 | LaHY | 74.9 | 30.4 | 3.1 | 5.3 | 0.2 | 35.6 | 44.9 |
| 5 | HML8 | 58.9 | 51.9 | 1.1 | 1.5 | 0.7 | 3.6 | 89.9 |
| 6 | HM20A | 76.1 | 30.4 | 7.1 | 10.5 | 0.5 | 2.3 | 49.4 |
| 7 | HM30A | 65.0 | 43.1 | 4.5 | 4.6 | 0.2 | 11.3 | 73.3 |

[a]Selectivity to sym-OHA plus THA, which is defined as the percentage of conversion.
[b]Products of ring-contraction isomerization and ring-opening cracking and subsequent dealkylation.

TABLE 4

Ring-Shift Isomerization of sym-OHP at 250° C. for 2 hours with TrMB Solvent

| Run | Catalyst type | Conv. mol % | Product (wt %) | | | | | Select.[a] % |
|---|---|---|---|---|---|---|---|---|
| | | | sym-OHA | THA | THP | DHP | Others[b] | |
| 8 | HY | 91.5 | 13.0 | 4.8 | 5.6 | 1.3 | 66.9 | 19.4 |
| 9 | NiHY | 58.5 | 47.7 | 1.8 | 4.4 | 0.3 | 4.2 | 84.6 |
| 10 | LaHY | 85.9 | 15.9 | 6.3 | 7.8 | 1.9 | 52.5 | 25.8 |
| 11 | HML8 | 58.7 | 52.4 | 1.1 | 1.3 | 1.6 | 1.5 | 91.1 |
| 12 | HM20A | 83.6 | 21.8 | 6.1 | 9.0 | | 65.0 | 33.4 |
| 13 | HM30A | 69.7 | 39.0 | 4.3 | 5.6 | 0.4 | 3.5 | 62.1 |

[a]Selectivity to sym-OHA plus THA, which is defined as the percentage of conversion.
[b]Products of ring-contraction isomerization and ring-opening cracking and subsequent dealkylation.

EXAMPLE 1

A horizontal-type stainless-steel autoclave having a volume of 25 mL was charged with 0.6 mMol (mili mole) of sym-OHP, 0.2 gram of a catalyst, and 1 mL (mili liter) of decalin solvent. The reactor was sealed, purged with $N_2$ for three times, and pressurized with 100 psi of nitrogen gas at room temperature. The charged reactor was plunged into a preheated fluidized sand bath heater at 250° C. and kept at that temperature for 2 hours with a vertical shaking of the reactor at about 200 cycles per minute. After the reaction, the reactor was cooled to room temperature. The contents of the microautoclave were washed out with acetone solvent and filtered. The used catalysts were washed with acetone solvent and dried at 120° C. for 2 hours. The liquid products in acetone solution were identified by using a capillary gas chromatograph (GC) coupled with a mass spectrometer (MS) using the GC-MS system consisting of a Hewlett-Packard 5890II GC and a Hewlett-Packard 5971A Mass Selective Detector. Both mass spectra and retention time were used in products identification. The yields of products were quantified using Perkin-Elmer 8500 GC, equipped with a 30 m×0.25 nun i.d. capillary column (DB-17) coated with 50% phenyl and 50% methylpolysiloxane.

Run 1 of Table 3 lists the results of this example using a proton-form Y zeolite catalyst, HY. Using HY, the products from sym-OHP isomerization are sym-OHA, 1,2,3,4-tetrahydroanthracene (THA), 1,2,3,4-tetrahydrophenanthrene (THP), 9,10-dihydrophenanth-rene (DHP), and other by-products such as those from cracking reactions and ring-contraction isomerization. The most desirable product is sym-OHA. THA is also a desirable product, as it is the intermediate in the conversion of sym-OHA to anthracene. The selectivity to anthracene derivatives (sym-OHA and THA) is defined as the percentage of the conversion. In the absence of a catalyst, sym-OHP does not undergo the isomerization to any significant extent at 250° C. However, the HY catalyst promoted the reaction and gave about a 78 percentage conversion of sym-OHP at 250° C. for 2 hours. The yield of sym-OHA is about 27 percent, based on the amount of sym-OHP charged into the reactor. The selectivity to anthracene derivatives (sym-OHA plus THA) is about 39 percent It should be mentioned that the commercial decalin solvent (from Aldrich Co.) used for the reaction of sym-OHP is a mixture of cis-decalin and trans-decalin isomers. We also found that during the reaction using acidic zeolite catalysts such as HY, the majority of cis-decalin is isomerized into trans-decalin. For example, the starting solvent is almost a 50:50 mixture of cis-decalin and trans-decalin. After 2 hours at 250° C. in the presence of sym-OHP and HY catalyst, there is about 83 percent trans-decalin and 7 percent cis-decalin. The other by-products make up the remainder.

EXAMPLE 2

With equipment and under the conditions generally as described in Example 1, an isomerization reaction was carried out using the iron ion-exchanged Y-zeolite, FeHY. The results are sununarized as Run 2 in Table 3. FeHy displayed certain degree of catalytic activity for the sym-OHP isomerization. However, it was less active as compared to HY in Example 1. This is due, at least in part, to the extensive dealumination that occurred during the ion-exchange process for preparing FeHY. The extensive dealumination resulted in substantial decrease in the catalyst acidity, as can be seen from the acidity numbers given in Table 1. The sym-OHP conversion and selectivity to anthracene derivatives were about 16 percent and 42 percent, respectively.

EXAMPLE 3

With equipment and under the conditions generally as described in Example 1, an isomerization reaction was carried out using the nickel ion-exchanged Y-zeolite, NiHY. The results are summarized as Run 3 in Table 3. NiHY displayed a much higher catalytic activity than FeHy in Example 2. The sym-OHP conversion was as high as about 83 percent. However, the yield of sym-OHA was about 21 percent based on sym-OHP, and the selectivity to anthracene derivatives was about 31 percent.

EXAMPLE 4

With equipment and under the conditions generally as described in Example 1, an isomerization reaction was carried out using the lanthanum ion-exchanged Y-zeolite, LaHY. The results are summarized as Run 4 in Table 3. LaHY showed a slightly lower activity for sym-OHP conversion, but a slightly higher selectivity, when compared with NiHY in Example 3. The sym-OHP conversion and the selectivity to anthracene derivatives were about 75 percent and 45 percent, respectively. The yield of sym-OHA was about 30 percent based on sym-OHP.

EXAMPLE 5

With equipment and under the conditions generally as described in Example 1, an isomerization reaction was carried out using a partially-dealuminated proton-form mordenite, HML8, which has a $SiO_2/Al_2O_3$ molar ratio of about 17. The results are summarized as Run 5 in Table 3. HML8 showed a considerably lower activity for sym-OHP conversion than the three acidic Y-zeolite catalysts (HY, NiHY, LaHY). However, the desired sym-OHA is the only major product with a yield of about 52 percent. The selectivity with HML8 is as high as about 90%. Because the selectivity is one of the most important factors to consider for the catalytic isomerization, the results with HML8 are highly desirable.

EXAMPLE 6

With equipment and under the conditions generally as described in Example 1, an isomerization reaction was carried out using a partially-dealuminated proton-form mordenite, HM20A, which has a $SiO_2/Al_2O_3$ molar ratio of about 20. The results are summarized as Run 6 in Table 3. HM20A showed a considerably higher activity for sym-OHP conversion than the HML8 in Example 5. However, the yield of the desired sym-OHA is much lower with HM20A (about 30 percent) than with HML8 (about 52 percent). The selectivity to anthracene derivatives is about 49 percent, which is lower than Example 5 using HML8, which is at about 90 percent.

EXAMPLE 7

With equipment and under the conditions generally as described in Example 1, an isomerization reaction was carried out using a partially-dealuminated proton-form mordenite, HM30A, which has a higher degree of dealumination with a $SiO_2/Al_2O_3$ molar ratio of about 35. The results are summarized as Run 7 in Table 3. HM30A showed a lower activity for sym-OHP conversion than the HM20A in Example 6. However, the yield of the desired sym-OHA is higher with HM30A (about 43 percent) than with HM20A (about 30 percent). Consequently, the selectivity to anthracene derivatives is higher with HM30A at about 73 percent than with HM20A at about 33 percent.

EXAMPLE 8

With equipment and under the conditions generally as described in Example 1, but with the decalin solvent replaced by mesitylene solvent, an isomerization reaction was carried out using the proton-form Y zeolite catalyst, HY. The results are summarized as Run 8 in Table 4. The sym-OHP conversion with mesitylene solvent (about 92 percent) is somewhat higher than that with the decalin solvent in Example 1 (about 78 percent). However, the selectivity to anthracene derivatives is lower in Example 8 (about 19 percent) than that in Example 1 (about 39 percent).

EXAMPLE 9

With equipment and under the conditions generally as described in Example 1, but with the decalin solvent replaced by mesitylene solvent, an isomerization reaction was carried out using the nickel ion-exchanged Y-zeolite, NiHY. The results are summarized as Run 9 in Table 4. There is considerable solvent effect with NiHY for sym-OHP isomerization. The selectivity of the sym-OHP isomerization to sym-OHA over NiHY is much higher (about 85 percent) in the presence of the aromatic solvent, mesitylene, than that obtained in the presence of the aliphatic solvent, decalin in Example 3 (about 31 percent). On the other hand, the sym-OHP conversion over NiHY with mesitylene solvent in Example 9 (about 59 percent) is lower than using decalin solvent as in Example 8 (about 83 percent). The high yield of sym-OHA (about 48 percent) in this run indicates that NiHY catalyze the reaction more selectively in the presence of the aromatic solvent, mesitylene.

EXAMPLE 10

With equipment and under the conditions generally as described in Example 1, but with the decalin solvent replaced by mesitylene solvent, an isomerization reaction was carried out using the lanthanum ion-exchanged Y-zeolite, LaHY, which has a $SiO_2/Al_2O_3$ molar ratio of 4.6. The results are summarized as Run 10 in Table 4. Compared to the run in the presence of decalin solvent (Example 4), LaHY showed a slightly higher activity for sym-OHP conversion (about 86 vs. about 75 percent but lower selectivity to sym-OHA (about 26 vs. about 45 percent) in the presence of mesitylene solvent.

EXAMPLE 11

With equipment and under the conditions generally as described in Example 1, but with the decalin solvent replaced by mesitylene solvent, an isomerization reaction was carried out using the partially-dealunfinated proton-form mordenite, HML8. The results are summarized as Run 11 in Table 4. The main product is sym-OHA with a yield of about 52 percent based on sym-OHP. The yield of all the other products are below 2 percent. The selectivity to the desired sym-OHA is as high as about 91 percent. Since the selectivity and activity of HML8 catalyst are at a similar level in the runs with either mesitylene or decalin, the type of solvent does not appear to affect the catalytic performance significantly at 250° C. for 2 hours. The results with HML8 are highly deskable, due to the high selectivity, which is one of the most important factors to consider for the catalytic isomerization of sym-OHP to sym-OHA.

Unlike the cases with decalin solvent, HML8 and NiHY showed similar catalytic activity in the presence of mesitylene solvent (Example 11 for HML8, and Example 9 for NiHY). The fact that HML8 displayed higher selectivity than any other catalysts at 250° C. in both aliphatic solvent (Example 5, decalin) and aromatic solvent (Example 11, mesitylene) suggests that HML8 has the characteristics most desirable to those required for the selective isomerization of sym-OHP to sym-OHA.

EXAMPLE 12

With equipment and under the conditions generally as described in Example 1, but with the decalin solvent replaced by mesitylene solvent, an isomerization reaction was carried out using a partially-dealuminated proton-form mordenite, HM20A, which has a $SiO_2/Al_2O_3$ molar ratio of about 20. The results are summarized as Run 12 in Table 4. Compared to the run in the presence of decalin solvent (Example 6), HM20A showed a slightly higher activity for sym-OHP conversion (about 84 vs. about 76 percent) but a lower selectivity to sym-OHA (about 33 vs. about 49 percent.

EXAMPLE 13

With equipment and under the conditions generally as described in Example 1, but with the decalin solvent replaced by mesitylene solvent, an isomerization reaction was carried out using a paxtially-dealuminated proton-form mordenite, HM30A, which has a higher degree of dealumination with a $SiO_2/Al_2O_3$ molar ratio of about 35. The results are surmnarized as Run 13 in Table 4. Compared to run 12 using HM20A in the presence of mesitylene solvent, run 13 using HM30A afforded a lower conversion (about 70 percent), but higher selectivity to sym-OHA (about 62 percent).

Although the invention has been disclosed with reference to preferred embodiments, it is to be understood that it is not limited to such embodiments and that various modifications of the invention are possible within the spirit and scope of the following claims.

What is claimed is:

1. An environmentally benign catalytic process for production of sym-octahydroanthracene from sym-octahydrophenanthrene by ring-shift isomerization, the steps comprising:

a. Contacting a feedstock that contains sym-octahydrophenanthrene with a proton-form mordenite or a partially dealuminated proton-form mordenite as a catalyst at elevated temperatures (100°–400° C.) under pressure of an inert gas or hydrogen and in the presence of an aliphatic or aromatic solvent for a period of time necessary for effective formation of sym-octahydroanthracene; and b. Separating the products of the reaction and the catalyst by filtration.

2. A process as claimed in claim 1, wherein said solvent is decalin or mesitylene.

3. An environmentally benign catalytic process for production of sym-octahydroanthracene from sym-octahydrophenanthrene by ring-shift isomerization, the steps comprising:

a. contacting a feedstock that contains sym-octahydrophenanthrene with a proton-form Y-zeolite or metal ion-exchanged proton-form Y-zeolite as a catalyst at elevated temperatures (100°–400° C.) under pressure of an inert gas or hydrogen and in the presence of decalin or mesitylene solvent for a period of time necessary for effective formation of sym-octahydroanthracene; and b. separating the products of the reaction and the catalyst by filtration; wherein said Y-zeolite has a $SiO_2/Al_2O_3$ molar ratio ranging from about 4.7 to about 69.5 and is selected from Ni ion exchanged Y-zeolites, Fe ion exchanged Y-zeolites, La ion exchanged Y-zeolites, and proton form Y-zeolites.

* * * * *